United States Patent [19]

Werner et al.

[11] Patent Number: 5,044,361
[45] Date of Patent: Sep. 3, 1991

[54] METHOD AND APPARATUS FOR REUSE OF ANESTHETICS

[75] Inventors: Olof Werner; Hans-Henrik Luttropp; Ronnie Thomasson, all of Lund; Georgios Psaros, Tullinge, all of Sweden

[73] Assignee: Zenova Aktiebolag and Siemens-Elema Aktiebolag, Sweden

[21] Appl. No.: 424,249

[22] PCT Filed: Apr. 12, 1988

[86] PCT No.: PCT/SE88/00184
§ 371 Date: Oct. 13, 1989
§ 102(e) Date: Oct. 13, 1989

[87] PCT Pub. No.: WO88/07876
PCT Pub. Date: Oct. 20, 1988

[30] Foreign Application Priority Data

Apr. 14, 1987 [SE] Sweden .............................. 8701547-5

[51] Int. Cl.⁵ .............................................. A61M 16/00
[52] U.S. Cl. ............................ 128/204.16; 128/203.12
[58] Field of Search ....................... 128/204.16, 205.12, 128/205.27, 205.28, 203.12; 55/DIG. 35, DIG. 33, 269, 316

[56] References Cited

U.S. PATENT DOCUMENTS

| | | | |
|---|---|---|---|
| 3,592,191 | 7/1971 | Jackson | 128/204.16 |
| 3,867,936 | 2/1975 | Kelley | 128/205.12 |
| 3,941,573 | 3/1976 | Chapel | 128/205.27 |
| 4,200,094 | 4/1980 | Gedeon et al. | 128/201.13 |

Primary Examiner—Aaron J. Lewis
Attorney, Agent, or Firm—Brooks & Kushman

[57] ABSTRACT

A method and an apparatus for reuse of anesthetics in inhalation anesthesia is described. In the method, fresh gas is mixed with highly concentrated anesthetic from an anesthetics evaporator (3) in a collector conduit (1) leading into and out of a patient, in such a way that, when the patient exhales, the exhalation gas is passed through an adsorption filter (5) disposed in the ingoing and outgoing collector conduit (1) and arranged distally relative to the outlet (4) from the anesthetics evaporator (3), as seen from the patient (2), the anesthetic not absorbed by the patient being adsorbed by an adsorption material (6) in the adsorption filter (5), while the rest of the exhalation gas leaves the apparatus, the adsorbed anesthetic being desorbed from the adsorption material (6) when the patient inhales and retransferred to the patient.

2 Claims, 2 Drawing Sheets

METHOD AND APPARATUS FOR REUSE OF ANESTHETICS

The present invention relates to a method and an apparatus for reuse of anesthetics in inhalation anesthesia.

Inhalation anesthesia is a common form of narcosis, and the anesthetics usually consist of simple halogenated hydrocarbons, paraffins or ethers which are in a liquid state at room temperature and are gasified prior to inhalation. Common anesthetics are Halotan or Fluotan (2-bromo-2-chloro-1,1,1-trifluoroethane), Enfluran or Efran (1,1,2-trifluoro-2-chloroethyl difluoromethyl ether), or Isofluran or Foren (2,2,2-trifluoro-1-chloroethyl difluoromethyl ether). The effect obtained from such halogenated hydrocarbons is normally increased by an addition of laughing gas ($N_2O$) at concentrations of 50–70 vol %.

The trend of development is towards more and more refined anesthetics which, however, suffer from the disadvantage of being obtainable only at high costs.

Furthermore, anesthetics are harmful to the operating staff if they leak out into the operating room.

The exhalation air from a patient contains nonabsorbed oxygen, laughing gas, water vapor, nonabsorbed anesthetic gas and 4–6 vol % $CO_2$.

Anesthetic gases can be administered to the patient by several different techniques and systems. The systems can be completely open, closed with re-breathing and $CO_2$ adsorption, or combinations thereof.

In one type of inhalation anesthesia, use is made of a respirator to which is connected a gasifier for anesthetic, emitting anesthetic gas at a predetermined concentration, e.g. 0–5 vol %, in for example a mixture of oxygen and laughing gas. The same gas flow as is supplied to the patient passes through the anesthetic gasifier. The anesthetic not absorbed by the patient passes to a suction outlet when the patient exhales and is lost. New gas containing anesthetic is supplied all the time, resulting in a high loss of expensive anesthetic in addition to the harmful effect on the operating staff.

In another system, the anesthetic gasifier is connected to the conduit leading into and out of the patient, and a small flow of fresh gas having a high concentration of anesthetic and emanating from the anesthetic gasifier is added to a larger gas flow from the respirator. Also in this system, the exhalation air, including anesthetic that has not been absorbed, is sucked out into the surroundings, and is constantly replaced by new fresh gas.

It is also possible to employ an anesthetic circuit permitting gas to be recirculated to the patient. In this case, an absorber is generally used, which eliminates the carbon dioxide produced by the patient. This method makes considerable gas savings possible, but requires, besides the absorber, special valve systems. Alternative ways of saving anesthetic are therefore of interest.

The object of the invention is to provide a method and an apparatus for reuse of anesthetics by which it is possible, at reasonable costs, to utilise high-priced anesthetics.

According to the invention, there is provided a new method and a new apparatus for saving anesthetics, in which the anesthetic not absorbed by the patient is adsorbed in a filter on exhalation and then desorbed out of the filter and reintroduced into the inhalation flow, i.e. a selective reflection of the anesthetic.

Figure 1:
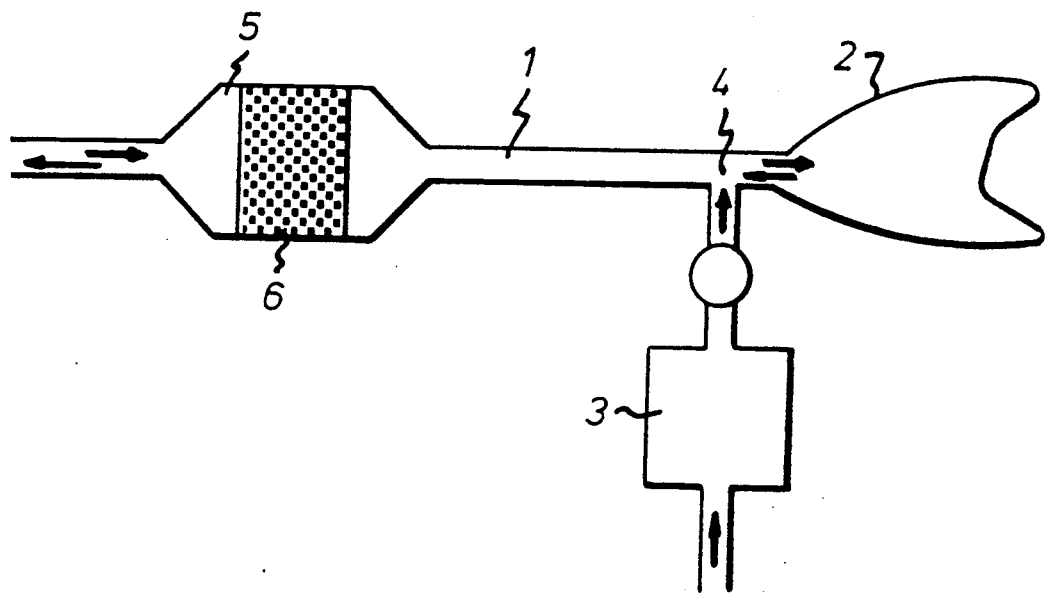
FIG. 1 illustrates an embodiment of the apparatus according to the invention, wherein the apparatus is connected to a respirator.

The invention thus comprises a method for reuse of anesthetics in inhalation anesthesia, wherein fresh gas is mixed with highly concentrated anesthetic from an anesthetics evaporator 3 in a collector conduit 1 leading into and out of a patient 2. The method is characterised in that, when the patient exhales, the exhalation gas is passed through an adsorption filter 5 disposed in the ingoing and outgoing collector conduit 1 and arranged distally relative to the outlet 4 from the anesthetics evaporator 3, as seen from the patient 2, the anesthetic being adsorbed by an adsorption material 6 in the adsorption filter 5, while the rest of the exhalation gas leaves the apparatus, the adsorbed anesthetic being desorbed from the adsorption material 6 when the patient inhales and retransferred to the patient.

The adsorption material of the filter should be such that it prefers the anesthetic to water and carbon dioxide. Examples of adsorption materials appropriate for use in the invention are inorganic silicon aluminium compounds, zeolites, active carbon, silicone plastics, silicone oil on a porous carrier, silica gels, highly porous plastic materials, microporous silicates etc.

The invention also comprises an apparatus for reuse of anesthetics in inhalation anesthesia, comprising a collector conduit 1 to be connected to a patient 2 and an anesthetics evaporator 3 which is connected to the collector conduit 1 via an outlet 4. The apparatus is characterised by an adsorption filter 5 containing an adsorption material 6 for adsorption and desorption of anesthetics and arranged in the collector conduit 1 distally relative to the outlet 4 from the anesthetics evaporator 3, as seen from the patient 2.

As in conventional installations for anesthesia, the apparatus according to the invention can also be provided with a separate device for absorption of $CO_2$.

Figure 2:
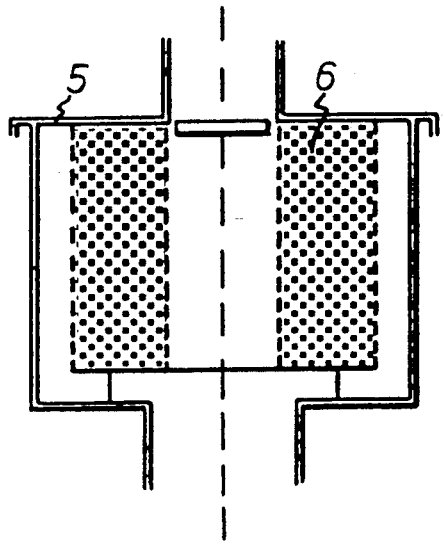
FIGS. 2–4 illustrate different embodiments of the adsorption filter appropriate for use in the apparatus according to the invention.
Figure 3:
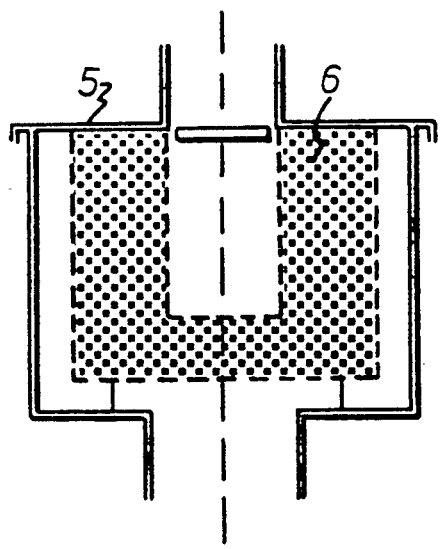
Figure 4:
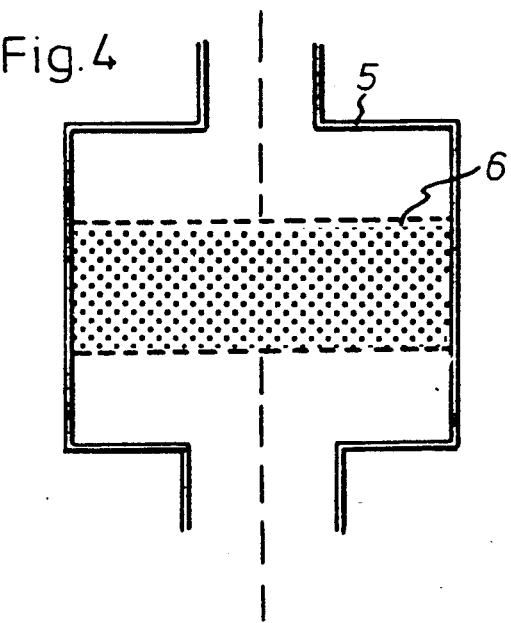

The filter used in the invention can be designed in any suitable manner. It can for example be a simple receptacle wherein the adsorption material is retained by means of some type of network arrangement, such that an ingoing and outgoing gas flow is compelled to pass through the adsorption material. Some examples of filter embodiments are shown in FIGS. 2–4.

The adsorption material can for example be in the form of pellets in order to facilitate variation of the pressure drop and the adsorption and desorption rates in the filter. The adsorption material can also be supported by a carrier; it can for example be attached to a paper carrier.

One type of adsorption material that has proved to be suitable are zeolites which are crystalline aluminium silicates. Thanks to their structure and chemical composition, these compounds are chemically stable and inert. Ultrastable, or dealuminised, zeolites have proved to be the best form of zeolites so far. Ultrastable zeolites have a high adsorption capacity for hydrophobic substances also in an environment which is mainly hydrophilic. This feature, and the fact that the zeolites to some extent have a low desorption energy, make a so-called reflection of the anesthetic possible.

When choosing the adsorption medium, it is important that the pressure drop across the filter and the dead volume are as low as possible. Furthermore, it is important that the anesthetic does not undergo a, for the purpose of the invention, essential chemical change when passing through the filter.

The invention can be used for all types of inhalation anesthesia, e.g. respirator controlled anesthesia, or anesthesia controlled by a bladder, and also for spontaneous respiration.

The invention will be described in more detail by means of the following Examples.

EXAMPLE 1

In this Example, a filter according to the invention, a so-called reflection filter, was used, comprising a receptacle of plastic material in which the adsorption material was disposed as a filter bed. Different geometric designs may be conceived for the filter, but for the sake of simplicity a substantially cylindrical receptacle of plastic material and with a diameter of about 5 cm was used, in which the adsorption material was disposed in the form of a layer with a thickness of 3 cm, retained between two nets which in cross-section were congruent with the receptacle. In the Example, the zeolites ultrastable Y, mordenite and silicalite were used, of which ultrastable Y proved to be the best. In order to prevent a possible transport of particles from the zeolite, a dust filter can be mounted on both sides of the reflection bed. The dead volume of the filter was >100 ml.

The anesthetics used were Isofluran and Halotan, the latter being less effective than Isofluran but considerably cheaper. No difference in the reflection rate between these two anesthetics could be observed.

In this experiment, the anesthetic was analysed before and after passage of the filter, and no significant chemical change in the anesthetics could be observed.

The result of the experiment was that about 80-95% of the anesthetic was recycled, that is a reflection rate of about 80-95% was obtained.

At a flow of 1 liter/s, a pressure drop of >2 cm water column (=0.2 kPa) was measured.

The reflection of other gases than the anesthetic, e.g. $H_2O$ and $CO_2$, was examined and found to be very low.

EXAMPLE 2

The experiments of Example 1 were repeated in animal tests. The filter was tested on pig. The anesthetic used was Isofluran which is a very expensive but excellent anesthetic.

The practical saving obtained in these animal experiments proved to be over 50% compared to the consumption of anesthetics in conventional narcosis.

To sum up, it will be appreciated that the invention makes it possible to utilise, without much regard to the cost involved, the most effective and safest anesthetic in a simple and uncomplicated manner.

What is claimed is:

1. Method for reuse of anesthetics in inhalation anesthesia, wherein fresh gas is mixed with highly concentrated anesthetic from an anesthetics evaporator (3) in a collector conduit (1) leading into and out of a patient (2), characterised in that, when the patient (2) exhales, the exhalation gas is passed in a first direction through an adsorption filter (5) disposed in the ingoing and outgoing collector conduit (1) and arranged distally relative to the outlet (4) from the anesthetics evaporator (3), as seen from the patient (2), the anesthetic gas not absorbed by the patient being adsorbed in gaseous form by an adsorption material (6) in the adsorption filter (5), while the rest of the exhalation gas leaves the apparatus, and when the patient inhales, the inhalation gas is passed in a second direction opposite the first direction through said adsorption filter (5), whereby the adsorbed anesthetic is desorbed from the adsorption material (6) and retransferred to the patient.

2. Apparatus for reuse of anesthetic gas in inhalation anesthesia, comprising a collector conduit (1) to be connected to a patient (2) and an anesthetics evaporator (3) which is connected to the collector conduit (1) via an outlet (4), characterised by an adsorption filter (5) containing an adsorption material (6) for adsorption and desorption of anesthetic gas in gaseous form and arranged in the collector conduit (1) distally relative to the outlet (4) from the anesthetics evaporator (3), as seen from the patient (2) thereby leading the exhalation gas through said adsorption filter (5) in a first direction and the inhalation gas through said adsorption filter (5) in a second direction opposite the first direction.

* * * * *